United States Patent [19]

Black et al.

[11] 4,006,231
[45] Feb. 1, 1977

[54] N-AMINOSULFENYLATED DERIVATIVES OF CARBOFURAN

[75] Inventors: Allan Lindsay Black, Dundas, Australia; Tetsuo Roy Fukuto, Riverside, Calif.

[73] Assignee: The Regents of the University of California, Berkeley, Calif.

[22] Filed: June 6, 1974

[21] Appl. No.: 476,767

Related U.S. Application Data

[63] Continuation-in-part of Ser. No. 378,700, July 12, 1973, abandoned.

[52] U.S. Cl. .................. 424/248.5; 424/250; 424/267; 424/274; 424/285; 260/247.15; 260/268 BC; 260/293.58; 260/326.36; 260/346.2 R
[51] Int. Cl.$^2$ ................. C07D 307/86; A01N 9/12
[58] Field of Search ................ 260/247.15, 293.58, 260/268 S, 326.36, 346.2 R; 424/248, 250, 267, 274, 285

[56] References Cited

UNITED STATES PATENTS

| | | | |
|---|---|---|---|
| 3,234,275 | 2/1966 | Malz et al. ................ | 260/293.85 |
| 3,344,153 | 9/1967 | Kuhle et al. ................ | 260/479 C |
| 3,564,605 | 2/1971 | Scharpf ................ | 424/285 |
| 3,663,594 | 5/1972 | Brown et al. ................ | 260/479 C |
| 3,699,122 | 10/1972 | Kohn ................ | 260/479 C |
| 3,709,907 | 1/1973 | Behforouz ................ | 260/268 S |
| 3,755,374 | 8/1973 | Zumach et al. ................ | 260/346.2 R |
| 3,812,174 | 5/1974 | Brown et al. ................ | 260/479 C |
| 3,843,689 | 10/1974 | Brown et al. ................ | 260/479 C |
| 3,847,951 | 11/1974 | Kohn et al. ................ | 260/342.6 |
| 3,897,463 | 7/1975 | Kohn ................ | 260/346.2 R |

FOREIGN PATENTS OR APPLICATIONS 71-00959   2/1973   South Africa

OTHER PUBLICATIONS

Fahmy et al., J. Agr. Food. Chem., 18, pp. 793–796, (1970).

*Primary Examiner*—Anton H. Sutto
*Assistant Examiner*—Michael Shippen
*Attorney, Agent, or Firm*—Robert L. Andersen; Henry R. Ertelt; Pauline Newman

[57] ABSTRACT

A new class of chemical compounds useful for the control of insects consists of (methyl)(aminosulfenyl)-carbamic acid esters of 2,3-dihydro-2,2-dimethyl-7-benzofuranol. The preparation of these compounds having a variety of (substituted-amino)sulfenyl groups, their physical properties, formulation, and use to control both household insects and crop pests are exemplified.

12 Claims, No Drawings

N-AMINOSULFENYLATED DERIVATIVES OF CARBOFURAN

This application is a continuation-in-part of copending application Ser. No. 378,700, filed July 12, 1973, now abandoned.

This invention pertains to the general field of pesticides and in particular to the area of insecticides for the control of both insects attacking crops and animals and insects which are disease vectors.

The compounds of this invention are N-aminosulfenyl derivatives of carbofuran, the common name of 2,3-dihydro-2,2-dimethyl-7-benzofuranyl methylcarbamate. Carbofuran, a potent insecticide, is described in U.S. Pat. No. 3,474,171, issued Oct. 21, 1969.

The N-aminosulfenyl derivatives of carbofuran are highly effective against certain pests and lower in mammalian toxicity than is carbofuran. These highly effective derivatives of carbofuran have not previously been described.

The new class of insecticidal compounds of this invention has the formula

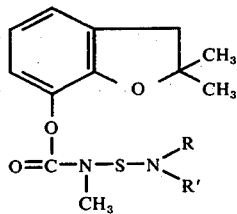

where R and R' may be the same or different, and each is alkyl of 1 to 8 carbon atoms which may contain an —O—, —S—, or —NR''— linkage, (where R'' is lower (1 to 4 carbons) alkyl, benzyl, or phenyl), cycloalkyl of 3 to 6 carbon atoms, or benzyl, or R and R'' taken together with the nitrogen form a heterocyclic ring of 5 to 8 members which may contain an —O—, —S—, or —NR''—, which heterocyclic ring may be substituted by one or more alkyl, aralkyl, aryl, or alkoxy groups. Preferred heterocyclic rings are pyrollidine, piperidine, morpholine, piperazine, and hexahydroazepine. Preferred heterocyclic ring substituents are lower alkyl, benzyl, phenyl or lower alkoxy, and the preferred number of such substituents is 1 or 2, except that there may be up to 4 methyl substituents. In the preferred compounds the total number of carbon atoms in heterocyclic ring substituents, if any, is 1 to 8 inclusive, the number of alkoxy substituents is no more than one, and the number of substituents on a carbon adjacent to the nitrogen bonded to the sulfenyl sulfur is no more than one.

The compounds of the invention are prepared by the reaction of a sulfenyl halide of the formula X—S—NRR', where X is halogen, preferably Br or Cl, with carbofuran in the presence of at least enough base to neutralize the HX formed. The reaction is conveniently carried out at about room temperature, for example 20°-25° C, but may be carried out at about 0° to 50° C.

The preparation and insecticidal properties of the compounds of this invention are illustrated in the following specific examples. Unless otherwise specified, all temperatures are in degrees centigrade, and concentration of liquid volume was carried out under the reduced pressure produced by a water aspirator.

EXAMPLE I

Synthesis of 2,3-Dihydro-2,2-dimethyl-7-benzofuranyl (Dimethylaminosulfenyl) (methyl)carbamate

A. Preparation of (dimethylamino)sulfenyl chloride

To a cold (−10°) solution of 25.7 g of sulfur dichloride (SCl$_2$) in 200 ml of diethyl ether was added, with vigorous stirring while maintaining the temperature at −10°, 22.5 g of dimethylamine. The precipitated dimethylamine hydrochloride was removed by filtration, the solid washed quickly with cold ether. The filtrate and ether wash were combined and the ether removed by gentle warming. The residue was distilled under reduced pressure to give 8.5 g of (dimethylamino)-sulfenyl chloride, b.p. 34°−36°/15 mm.

B. Reaction of (dimethylamino)sulfenyl chloride with carbofuran

A mixture of 16 g of carbofuran and 8.5 g of (dimethylamino)sulfenyl chloride in 50 ml of pyridine was allowed to stand at room temperature for about 18 hours. The mixture was poured into water, the aqueous mixture extracted with chloroform, the extracts washed with dilute hydrochloric acid, followed by water and saturated sodium chloride solution. Concentration under reduced pressure gave an oil which was found by nuclear magnetic resonance spectroscopy to contain about 20% unreacted carbofuran. This oil was subjected to column chromatography on silica gel using diethyl etherhexane (3:1) as eluting solvent to obtain 2,3-dihydro2,2-dimethyl-7-benzofuranyl (dimethylaminosulfenyl)(methyl)carbamate (Analysis: Calc'd for C$_{14}$H$_{20}$N$_2$O$_3$S: C 56.76; H 6.76; Found: C 56.94; H 7.26.

EXAMPLE II

Synthesis of 2,3-Dihydro-2,2-dimethyl-7-benzofuranyl (Methyl)(morpholinosulfenyl)carbamate

A. Preparation of morpholinosulfenyl chloride

A solution of 17.2 g of morpholine in 250 ml of diethyl ether was cooled to −10° in an ice-salt bath and to the cold solution was added a solution of 4.65 g of sulfur dichloride in 50 ml of dry diethyl ether. Stirring was continued for 1 hour at −10°, then the mixture was allowed to warm to room temperature. The precipitated morpholine hydrochloride was removed by filtration, the filtrate was concentrated and the residue distilled to give 4.8 g of morpholinosulfenyl chloride, b.p. 60°−62°/1.0 mm.

B. Reaction of morpholinosulfenyl chloride with carbofuran

A mixture of 6.6 g of carbofuran and 4.8 g of morpholinosulfenyl chloride in 40 ml of pyridine was allowed to stand at room temperature for about 18 hours. The mixture, which contained solid pyridine hydrochloride, was poured into water and the aqueous mixture extracted with diethyl ether. The ether extract was washed with dilute acid, then with water and with saturated sodium chloride solution and dried. Evaporation of the ether gave 6.1 g of 2,3-dihydro-2,2-dimethyl-7-benzofuranyl (methyl)(morpholinosulfenyl)carbamate, m.p. 75°−78°. Recrystallization from hexane-diethyl ether increased the melting point to 89°.

Analysis: Calc'd for $C_{16}H_{22}N_2O_4S$: C 56.78; H 6.55; Found: C 57.47; H 6.54.

EXAMPLE III

Toxicity to Houseflies

Toxicity of the compounds of the present invention to houseflies was tested using the technique described by March and Metcalf (Bull. Calif. State Dept. Agr. 38, No. 2, 93–101 [1949]): Solutions of test compounds in acetone were prepared at a range of concentrations. Adult female houseflies (*Muscadomesticus*) were treated with one drop of acetone solution, applied to the prothorax, using a syringe calibrated to deliver 1.00 ±0.05 mm³ drops. Twenty flies were treated at each dosage, each test compound was applied at 8 to 10 dosage levels. Each test was replicated three times. Following treatment, each lot of flies was confined in paper-lined one-quart cylindrical cartons, the solid ends of which had been replaced with wire screen. A one-inch square of cotton saturated with 40% sugar solution was provided for food in each carton. The cartons of flies were held in a constant temperature chamber at 60° F and 60% relative humidity for 24 hours before mortality counts were made. Flies totally unable to make crawling or walking movements were counted as dead. $LD_{50}$ values were calculated in the conventional manner. The results are presented in Table 1. The test compounds were approximately 0.4 to 0.7 times as toxic as the parent carbofuran.

EXAMPLE IV

Toxicity to Mosquitoes

Toxicity of the compounds of the present invention to mosquitoes was tested using the technique described by Mulla, Metcalf and Geib (Mosquito News 28, No. 2, 236 [1966]): A 1% (w/v) stock solution was prepared by dissolving the test compound in acetone. The appropriate amount of stock solution was added with stirring to 100 ml of tap water and 20–25 fourth-instar larvae of Culex fatigans were placed in the solution. After 24 hours, the counts were taken. Larvae not able to rise to the surface on touch were counted as dead. Each concentration was run in duplicate and each material was run on two or three different days. The average percent mortality was plotted against the logarithm of the concentration (in ppm) and the $LC_{50}$ value determined by inspection. The results are presented in Table 1. The compounds tested were slightly more toxic to mosquitoes than the parent carbofuran.

EXAMPLE V

Toxicity to Mice

Acute oral toxicity of the compounds of the present invention to mice was determined after the manner of Hollingworth, Fukuto and Metcalf (J. Agr. Food Chem. 15, 235 [1967]): Solutions of the compounds at each of a series of concentrations were prepared in olive oil or propylene glycol as solubility required. A dose of 0.25 ml of each solution was administered to each of four female white Swiss mice using the "bolus"-tipped syringe. The mice were closely observed during the one to two hours immediately after treatment, during which most of the mortality occurred. Final mortality determinations were made 48 hours after treatment. Results are presented in Table 1. $LD_{50}$ values were numerically from five to ten times greater than that obtained for the parent carbofuran, indicating that the compounds of the present invention are less toxic to mammals than the parent.

Table 1

| Compound of Example | Toxicity to Houseflies, Mosquitoes, Mice | | |
|---|---|---|---|
| | Houseflies $LD_{50}$ (mg/kg) | Mosquitoes $LC_{50}$ (ppm) | Mice $LD_{50}$ (mg/kg) |
| I | About 15.0 | 0.027 | 10–20 |
| II | About 10.5 | 0.048 | 10–20 |
| Carbofuran | About 6.7 | 0.052 | About 2 |

EXAMPLE VI

Toxicity to Crop Pests

Initial Contact Activity: One-half gram of test compound was dissolved in 40 ml of acetone and this solution was dispersed in 360 ml of water containing one drop of isooctylphenyl polyethoxyethanol. An aliquot of this solution was diluted with water to provide a solution containing 1250 ppm of active ingredient. Test organisms and techniques were as follows: The activities against the Mexican bean beetle (*Epilachna varivestis* Muls.) and the southern army worm (*Prodenia eridana* [Cram.]) were evaluated by dipping the leaves of pinto bean plants into the test solution and infesting the leaves with the appropriate immature-form insects when the foliage had dried; the activity against the pea aphid (*Macrosiphum pisi* [Harris]) was evaluated on broad bean plants whose leaves were dipped before infestation with adult aphids; the activity against the two-spotted spider mite (*Tetranychus urticae* [L.]) was evaluated on pinto bean plants whose leaves were dipped after infestation with adult mites; the activities against the milkweed bug (*Oncopeltus fascinatus* [Dallas]) and the plum curculio (*Conotrachelus nenuphar* [Herbst]) were evaluated by spraying the test solutions into glass dishes containing the adult insects; the activities against the granary weevil (*Sitophilus granarius* [L.]) and the confused flour beetle (*Tribolium confusum* [duVal]) were evaluated by introducing the insects into glass dishes which had been previously sprayed with test solution and allowed to dry. All organisms in the test were maintained in a holding room at 80° F and 50% relative humidity for an exposure period of 48 hours. At this time, the dead and living insects (or mites) were counted and the percent kill was calculated. Results of these tests are summarized in Table 2, which shows the compounds to be effective against mites and a broad range of insects.

Residual Contact Activity: The residual contact activity of the compounds was determined on the same organisms using the technique described above, except that in each case the treated surface was allowed to dry and was exposed to normal light and air for seven days before introduction of the mites or insects. Results of these tests are summarized in Table 2. The compounds show a high order of residual activity toward the test insects.

Table 2

| Pest | Toxicity of Compounds I and II to Crop Pests (% Kill at 1250 ppm) | | | |
|---|---|---|---|---|
| | Initial | | Residual (7-day) | |
| | I | II | I | II |
| BB | 100 | 100 | 95 | 100 |
| AW | 100 | 100 | 80 | 83 |
| PA | 100 | 100 | 95 | 100 |

Table 2-continued

Toxicity of Compounds I and II to Crop Pests
(% Kill at 1250 ppm)

| Pest | Initial | | Residual (7-day) | |
|---|---|---|---|---|
| | I | II | I | II |
| SM | 100 | 97 | 3 | 4 |
| MWB | 100 | 100 | 100 | 100 |
| PC | 100 | 100 | 5 | 100 |
| GW | 100 | 100 | 63 | 100 |
| FB | 100 | 100 | 0 | 0 |

BB: Mexican bean beetle
AW: southern army worm
PA: pea aphid
SM: two-spotted spider mite
MWB: milkweed bug
PC: plum curculio
GW: granary weevil
FB: confused flour beetle

EXAMPLE VII

Systemic Insecticidal Activity

The soil-watering technique was utilized to measure systemic activity. Test organisms were Mexican bean beetle, southern army worm, pea aphid, and two-spotted spider mite on plants as described in Example VI. Using appropriate precautions to avoid contamination of the test plant surfaces, 25 ml of a test solution, prepared as in Example VI so as to contain 156 ppm, was poured evenly over the surface of the soil in which the plant was growing. The treated plants were maintained under normal growing conditions for 3 days to permit translocation of the toxicant, after which the leaves were infested. Two days after infestation, counts of living and dead insects were made. These results are summarized in Table 3. A high order of systemic activity is characteristic of compounds of the present invention.

Table 3

Systemic Toxicity to Crop Insects

| Insect | (% Kill at 156 ppm) Compound I | Compound II |
|---|---|---|
| BB | 100 | 100 |
| AW | 100 | 100 |
| PA | 100 | 100 |
| SM | 73 | 76 |

BB: Mexican bean beetle
AW: southern army worm
PA: pea aphid
SM: two-spotted spider mite By the method exemplified in Examples I and II the following compounds were prepared. Each was recovered as a heavy oil which could not be distilled.

EXAMPLE VIII 2,3-Dihydro-2,2-dimethyl-7-benzofuranyl (2,6-dimethylmorpholinosulfenyl)(methyl)carbamate Analysis: Calc'd $C_{18}H_{26}N_2O_4S$: C 58.99; H 7.15; N 7.64; Found: C 59.95; H 7.45; N 7.54.

EXAMPLE IX 2,3-Dihydro-2,2-dimethyl-7-benzofuranyl (dipropylaminosulfenyl)methyl)carbamate Analysis: Calc'd $C_{18}H_{28}N_2O_3S$: C 61.33; H 8.00; N 7.95; Found: C 61.61; H 8.22; N 7.73.

EXAMPLE X 2,3-Dihydro-2,2-dimethyl-7-benzofuranyl (methyl)(4-methylpiperidinosulfenyl)carbamate Analysis: Calc'd $C_{18}H_{25}N_2O_3S$: C 61.86; H 7.21; N 8.02; Found: C 61.84; H 7.06; N 7.88.

EXAMPLE XI 2,3-Dihydro-2,2-dimethyl-7-benzofuranyl (methyl)(piperidinosulfenyl)carbamate Analysis: Calc'd $C_{17}H_{24}N_2O_3S$: C 60.69; H 7.19; N 8.33; Found: C 59.47; H 7.47; N 8.20.

EXAMPLE XII 2,3Dihydro-2,2-dimethyl-7-benzofuranyl (methyl)(3-methylpiperidinosulfenyl)carbamate Analysis: Calc'd $C_{18}H_{26}N_2O_3S$: C 61.68; H 7.48; N 7.99; Found: C 61.92; H 7.31; N 7.92.

EXAMPLE XIII 2,3Dihydro-2,2-dimethyl-7-benzofuranyl (methyl)[(methyl)(cyclohexyl)aminosulfenyl]carbamate Analysis: Calc'd $C_{19}H_{28}N_2O_3S$: C 62.60; H 7.74; N 7.96; Found: C 62.11; H 7.79; N 7.76.

EXAMPLE XIV 2,3-Dihydro-2,2-dimethyl-7-benzofuranyl (4-benzylpiperidinosulfenyl)(methyl)carbamate Analysis: Calc'd $C_{24}H_{30}N_2O_3S$: C 67.58; H 7.09; N 6.57; Found: C 67.40; H 7.29; N 6.46.

EXAMPLE XV 2,3Dihydro-2,2-dimethyl-7-benzofuranyl (dihexylaminosulfenyl)methyl)carbamate Analysis: Calc'd $C_{24}H_{40}N_2O_3S$: C 66.02; H 9.23; N 6.41; Found: C 66.21; H 9.50; N 6.39.

EXAMPLE XVI 2,3-Dihydro-2,2-dimethyl-7-benzofuranyl dibutylaminosulfenyl(methyl)carbamate Analysis: Calc'd $C_{20}H_{32}N_2O_3S$: C 63.12; H 8.48; N 7.36; Found: C 63.10; H 8.70; N 7.09.

EXAMPLE XVII 2,3-Dihydro-2,2-dimethyl-7-benzofuranyl (methyl)(4-phenylpiperidinosulfenyl)carbamate Analysis: Calc'd $C_{23}H_{28}N_2O_3S$: C 66.96; H 6.84; N 6.79; Found: C 67.14; H 6.75; N 6.58.

EXAMPLE XVIII 2,3-Dihyro-2,2-dimethyl-7-benzofuranyl (diisobutylaminosulfenyl(methyl)carbamate Analysis: Calc'd $C_{20}H_{32}N_2O_3S$: C 63.12; H 8.48; N 7.36; Found: C 63.07; H 8.73; N 7.47.

EXAMPLE XIX 2,3-Dihydro-2,2-dimethyl-7-benzofuranyl (4,4-dimethylpiperidinosulfenyl)methyl)carbamate Analysis: Calc'd $C_{19}H_{28}N_2O_3S$: C 62.61; H 7.74; N 7.69; Found: C 62.90; H 7.54; N 7.82.

EXAMPLE XX 2,3-Dihydro-2,2-dimethyl-7-benzofuranyl [(benzyl)(ethyl)aminosulfenyl](methyl)carbamate Analysis: Calc'd $C_{21}H_{27}N_2O_3S$: C 65.08; H 7.02; N 7.23; Found: C 65.07; H 6.92; N 7.22.

Each of the compounds of Examples VIII through XX was tested against at least six crop pests by the method of Example VI, and each was found to have a high order of pesticidal activity.

The insecticidal (methyl) (aminosulfenyl)carbamic acid esters of 2,3-dihydro-2,2-dimethyl-7-benzofuranol may be formulated with the usual additives and extenders used in the preparation of insecticidal compositions. The toxicants of this invention, like most insecticidal agents, are generally not applied full strength, but are incorporated with the adjuvants and carriers normally employed for facilitating the dispersion of active ingredients, recognizing the accepted fact that the formulation and mode of application of a toxicant may affect the activity of the material. The present compounds may be applied, for example, as a spray, dust, or granule, to the area in which pest control is desired, the choice of application varying of course with the type of insect and the environment. Thus, these (aminosulfenyl)(methyl)carbamic esters of 2,3-dihydro-2,2-dimethyl-7-benzofuranol may be formulated as granules of large particle size, as powdery dusts, as wettable powders, as emulsifiable concentrates, as solutions, and the like.

Dusts are admixtures of the active ingredients with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as dispersants and carriers for the toxicant. These finely divided solids have an average particle size of less than about 50 microns. A typical dust formulation useful herein contains 10.0 parts of 2,3-dihydro-2,2-dimethyl-7-benzofuranyl (methyl)(morpholinosulfenyl)carbamate, 30.0 parts of bentonite clay, and 60.0 parts of talc.

The compounds of the present invention may be made into liquid concentrates by solution or emulsion in suitable liquids, and into solid concentrates by admixtures with talc, clays and other known solid carriers used in the insecticide art. The concentrates are compositions containing about 5–50% toxicant, and 95–50% inert material which includes dispersing agents, emulsifying agents, and wetting agents. The concentrates are diluted for practical application, with water or other liquid for sprays or with additional solid carrier for use as dusts. Typical carriers for solid concentrates (also called wettable powders) include fuller's earth, kaolin clays, silicas, and other highly absorbent, readily wet iorganic diluents. A solid concentrate formulation useful herein contains 1.5 parts each of sodium lignosulfonate and sodium laurylsulfate as wetting agents, 25.0 parts of 2,3-dihydro-2,2-dimethyl-7-benzofuranyl (dimethylaminosulfenyl)(methyl) carbamate and 72.0 parts of bentonite clay.

Useful liquid concentrates include the emulsifiable concentrates, which are homogeneous liquid or paste compositions readily dispersed in water or other dispersant, and may consist entirely of the toxicant with a liquid or solid emulsifying agent, or may also contain a liquid carrier such as xylene, heavy aromatic naphthas, isophorone and other nonvolatile organic solvents. For application, these concentrates are dispersed in water or other liquid carrier, and normally applied as a spray to the area to be treated.

Typical wetting, dispersing or emulsifying agents used in insecticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols: polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surfaceactive agent, when used, normally comprises from 1–15% by weight of the insecticidal composition.

Other useful formulations include simple solutions of the active ingredient in a solvent in which it is completely soluble at the desired concentration, such as acetone or other organic solvents.

The concentration of the toxicant in the dilution generally used for application is normally in the range of about 2% to about 0.001%. Many variations of spraying and dusting compositions in the art may be used, by substituting a compound of this invention into compositions known or apparent to the art.

Insecticidal compositions may be formulated and applied with other active ingredients, including other insecticides, nematicides, acaricides, fungicides, plant regulators, fertilizers, etc. In applying the chemicals, it is obvious that an effective amount and concentration of (aminosulfenyl)(methyl)carbamic acid ester of 2,3-dihydro-2,2-dimethyl-7-benzofuranol should be employed.

It is apparent that many modifications may be made in the structure, preparation, formulation and application of the compounds of this invention, without departing from the spirit and scope of the invention and of the following claims.

We claim:
1. A compound of the formula

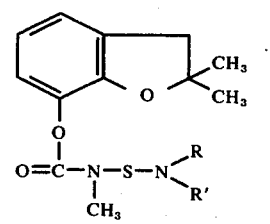

where R and R' may be the same or different and each is alkyl of 1 to 8 carbon atoms, cycloalkyl of 3 to 6 carbon atoms, or benzyl, or R and R' taken together with the nitrogen form a pyrollidine, piperidine, morpholine, piperazine, or hexahydroazepine heterocyclic ring which may have one or more substituents selected from lower (1 to 4 carbons) alkyl, benzyl, phenyl, or lower alkoxy, with the provisos that (1) the total number of carbon atoms in said substituents is 1 to 8 inclusive, (2) the number of alkoxy substituents on the heterocyclic ring is zero or one, and (3) the number of substituents on a carbon adjacent to the nitrogen atom bonded to the sulfenyl sulfur is zero or one.

2. A compound of claim 1 in which R and R' are alkyl of 1–8 carbon atoms or taken together form a pyrrolidine, piperidine, morpholine, piperazine, or hexahydroazepine heterocyclic ring.

3. The compound of claim 2 which is 2,3-dihydro-2,2-dimethyl-7-benzofuranyl (dimethylaminosulfenyl)-(methyl)carbamate.

4. The compound of claim 2 which is 2,3-dihydro-2,2-dimethyl-7-benzofuranyl (methyl)(morpholinosulfenyl)carbamate.

5. The compound of claim 2 which is 2,3-dihydro-2,2-dimethyl-7-benzofuranyl (methyl)(piperidinosulfenyl)carbamate.

6. A compound of claim 1 in which the heterocyclic ring formed by R and R' is a piperidine or morpholine ring.

7. A compound of claim 6 in which any substituents on the heterocyclic ring are lower alkyl, benzyl, phenyl, or lower alkoxy.

8. A compound of claim 7 in which any substituent is methyl, and there may be up to and including three methyl substituents on the ring.

9. The compound of claim 7 which is 2,3-dihydro-2,2-dimethyl-7-benzofuranyl (methyl)(3-methyl-piperidinosulfenyl)carbamate.

10. The compound of claim 7 which is 2,3-dihydro-2,2-dimethyl-7-benzofuranyl (4,4-dimethyl-piperidinosulfenyl)(methyl)carbamate.

11. An insecticidal composition comprising an insecticidally effective amount of a compound of claim 1 in admixture with an carrier.

12. The method of controlling insects which comprises applying to the situs of infestation an insecticidally effective amount of a compound of claim 1.

* * * * *

UNITED STATES PATENT OFFICE
CERTIFICATE OF CORRECTION

Patent No. 4,006,231          Dated February 1, 1977

Inventor(s) Allan L. Black et al.

It is certified that error appears in the above-identified patent and that said Letters Patent are hereby corrected as shown below:

Column 1, line 39, "R"" should read --R'--
Column 2, line 34, "2,3-dihydro2,2-dimethyl-7-benzofuranyl" should read --2,3-dihydro-2,2-dimethyl-7-benzofuranyl--
Column 5, line 65, "(dipropylaminosulfenyl)methyl)carbamate" should read --(dipropylaminosulfenyl)(methyl)carbamate--
Column 6, line 17, "2,3Dihydro-2,2-dimethyl-7-benzofuranyl" should read --2,3-Dihydro-2,2-dimethyl-7-benzofuranyl--
Column 6, line 23, "2,3Dihydro-2,2-dimethyl-7-benzofuranyl (methyl)" should read --2,3-Dihydro-2,2-dimethyl-7-benzofuranyl(methyl)--
Column 6, line 27, "7.96;" should read --7.69;--
Column 6, line 37, "2,3Dihydro-2,2-dimethyl-7-benzofuranyl" should read --2,3-Dihydro-2,2-dimethyl-7-benzofuranyl--
Column 6, line 38, "(dihexylaminosulfenyl)methyl)carbamate" should read --(dihexylaminosulfenyl)(methyl)carbamate--
Column 6, line 45, "dibutylaminosulfenyl(methyl)carbamate" should read --(dibutylaminosulfenyl)(methyl)carbamate--
Column 6, line 57, "2,3-Dihyro-2,2-dimethyl-7-benzofuranyl" should read --2,3-Dihydro-2,2-dimethyl-7-benzofuranyl--
Column 6, line 58, "(diisobutylaminosulfenyl(methyl)carbamate" should read --(diisobutylaminosulfenyl)(methyl)carbamate--
Column 6, line 66, "(4,4-dimethylpiperidinosulfenyl)methyl)carbamate" should read --(4,4-dimethylpiperidinosulfenyl)(methyl)carbamate

UNITED STATES PATENT OFFICE
CERTIFICATE OF CORRECTION

Patent No. 4,006,231      Dated February 1, 1977

Inventor(s) Allan L. Black et al.

It is certified that error appears in the above-identified patent and that said Letters Patent are hereby corrected as shown below:

Column 7, line 57, "iorganic diluents." should read --inorganic diluents.--
Column 8, line 10, "polyvinyl alcohols:" should read --polyvinyl alcohols;--

Signed and Sealed this thirtieth Day of August 1977

[SEAL]

Attest:

RUTH C. MASON
Attesting Officer

C. MARSHALL DANN
Commissioner of Patents and Trademarks